(12) United States Patent
Matulic-Adamic

(10) Patent No.: US 6,268,534 B1
(45) Date of Patent: Jul. 31, 2001

(54) PROCESS FOR THE SYNTHESIS OF N,N-DIOLEYL-N,N-DIMETHYLAMMONIUM CHLORIDE

(75) Inventor: Jasenka Matulic-Adamic, Boulder, CO (US)

(73) Assignee: Ribozyme Pharmaceuticals, Inc., Boulder, CO (US)

( * ) Notice: Subject to any disclaimer, the term of this patent is extended or adjusted under 35 U.S.C. 154(b) by 0 days.

(21) Appl. No.: 09/253,258

(22) Filed: Feb. 19, 1999

Related U.S. Application Data

(60) Provisional application No. 60/075,647, filed on Feb. 23, 1998.

(51) Int. Cl.[7] ................................................. C07C 209/12
(52) U.S. Cl. ............................................................. 564/296
(58) Field of Search ............................................. 564/296

(56) References Cited

U.S. PATENT DOCUMENTS 5,785,992 * 7/1998 Ansell et al. ........................ 424/450

FOREIGN PATENT DOCUMENTS

| 2300381 | 12/1990 | (JP) . |
| 4108172 | 4/1992 | (JP) . |
| 4222280 | 8/1992 | (JP) . |
| 7-3650 | 1/1995 | (JP) . |
| 7-69837 | 3/1995 | (JP) . |
| 7330551 | 12/1995 | (JP) . |
| 7330552 | 12/1995 | (JP) . |
| 8-48994 | 2/1996 | (JP) . |
| 8048995 | 2/1996 | (JP) . |
| 96/04964 | 2/1996 | (WO) . |
| 96/10390 | 4/1996 | (WO) . |

OTHER PUBLICATIONS

Wasan et al., "Plasmid DNA is protected against ultrasonic cavitation–induced damage when complexed to cationic liposomes," *Can J. Pharm. Sci* 85:427–433 (1996).
Reimer et al., "Formation of novel hydrophobic complexes between cationic lipids and plasmid DNA," *Biochemistry* 34:12877–12883 (1995).

* cited by examiner

*Primary Examiner*—Peter O'Sullivan
(74) *Attorney, Agent, or Firm*—Lyon & Lyon LLP

(57) ABSTRACT

A novel process for the synthesis of N,N-dioleyl-N,N-dimethylammonium chloride (DODAC) is described.

19 Claims, 1 Drawing Sheet

Figure 1:
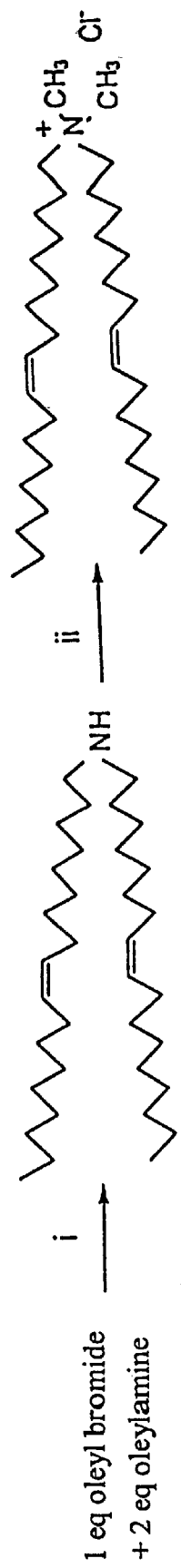

Reagents: I, heating; ii, CH$_3$I/KHCO$_3$/methanol, ion exchange

PROCESS FOR THE SYNTHESIS OF N,N-DIOLEYL-N,N-DIMETHYLAMMONIUM CHLORIDE

CROSS-REFERENCE TO RELATED APPLICATIONS

This application claims priority to U.S. Provisional Application No. 60/075,647 entitled, "NOVEL PROCESS FOR THE SYNTHESIS OF N,N-DIOLEYL-N,N-DIMETHYLAMMONIUM CHLORIDE", Jasenka Matulic-Adamic, filed on Feb. 23, 1998, which is hereby incorporated by reference herein in its entirety, including any drawings.

FIELD OF THE INVENTION

This invention relates to a novel method of the synthesis of N,N-Dioleyl-N,N-Dimethylammonium Chloride (DODAC).

BACKGROUND OF THE INVENTION

The following is a brief description of the synthesis of a lipid compound. This summary is not meant to be complete but is provided only for understanding of the invention that follows. This summary is not an admission that any of the work described below is prior art to the claimed invention.

N,N-Dioleyl-N,N-Dimethylammonium Chloride (DODAC) is an amphipathic compound which has been used for a variety of purposes. Several laboratories have reported the use of DODAC for the transfection of nucleic acid molecules into cells and mammalian organs, either independently or mixed with another compound (Ansell et al., International PCT Publication No. WO 96/10390; Wheeler et al, International PCT Publication No. WO 96/04964; Wasan et al, 1996, *Can. J. Pharm. Sci.* 85, 427–33; Reimer et al., 1995, *Biochemistry* 34, 12877–83).

DODAC has also been described as a component of certain liquid detergents (Inoe et al., Japanese Patent Application No. JP 08048995); and Inoe et al., Japanese Patent Application No. JP 94-184925), for use in hair treatment (Kaji et al., Japanese Patent Application No. JP 07330552; Yamamoto et al., Japanese Patent Application No. JP 07330551; and Ikeda et al., Japanese Patent Application No. JP 93-235708) and as a fabric softener (Umezawa et al., Japanese Patent Application No. JP 93-168582; Ide et al., Japanese Patent Application No. JP 05059670; Kobauashi et al., Japanese Patent Application No. JP 04222280; Takeuchi et al., Japanese Patent Application No. JP 04108172; and Inokoshi, Japanese Patent Application No. JP 02300381).

Ansell et al., supra describes two methods for the synthesis of DODAC. The first process involves the synthesis of DODAC through the formation of two intermediates for a total of three steps: 1) formation of N-oleyloleoylamide from oleylamine and oleic acid; 2) reduction of N-oleyloleoylamide to dioleylamine; and 3) methylation of dioleylamine to form DODAC.

The second method described in Ansell et al., is a two step approach which uses flammable dimethylamine gas in the first step. The quaternization reaction of this reaction scheme is conducted in the heterogeneous mixture of chloroform and aqueous NaOH at reflux temperature for 16 hours followed by treatment in concentrated hydrochloric acid and repeated extraction through chloroform.

SUMMARY OF THE INVENTION

Methods for the synthesis of DODAC described in the art involve time consuming multiple-step reactions, and in certain instances utilize caustic or harsh chemicals during synthesis and extraction. In the present invention, Applicant describes a novel, fast, cheap and an efficient method for the synthesis of N,N-Dioleyl-N,N-Dimethylammonium Chloride (DODAC). Additionally, the process described in the present invention utilizes non-flammable liquid reagents that are safer to prepare and easier to scale up. The new process also limits the exposure of the DODAC to harsh chemicals, which may potentially increase the yield of synthesis.

In a preferred embodiment, the invention features a process for the synthesis of N,N-dioleyl-N,N-dimethylammonium chloride (DODAC) comprising the steps of oleylation, where oleyl bromide is contacted with oleylamine under conditions suitable for the formation of N,N-dioleylamine; and methylation of the resulting N,N-dioleylamine under conditions suitable for the formation of DODAC.

Oleylation of the amine group on oleylamine occurs through nucleophilic attack by the amine group to form N,N-dioleylamine as shown below:

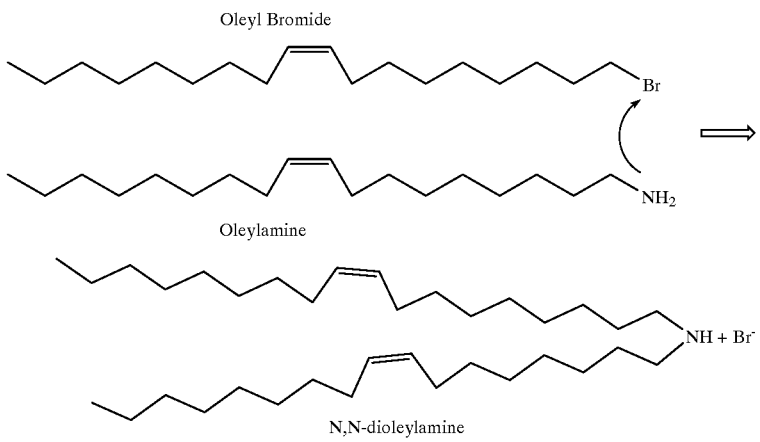

By "oleylation" is meant, formation of a covalent bond between a hydrocarbon molecule consisting of 18 carbon atoms with a double bond at delta 9 (oleyl group) with a separate atom or molecule.

By "conditions suitable for oleylation" is meant, reaction conditions including reaction temperature of preferably between 80° C. and 150° C., specifically between 90° C. and 150° C., more specifically between 100° C. and 150° C.; a reaction time of preferably between 30 and 90 minutes specifically between 45 and 75 minutes, more specifically between 50 and 60 minutes. Those skilled in the art will recognize that the reaction temperature and time may be varied without significantly affecting the reaction.

By "nucleophilic attack" is meant, a reaction where the nucleophile (the group that forms a new bond with carbon) attaches to a carbon atom displacing the leaving group.

In another preferred embodiment, oleylation is carried out in the presence of oleyl methone sulfonate or oleyl p-toluene sulfonate or the like, in place of oleyl bromide.

In yet another preferred embodiment, N,N-dioleylamine is reacted with methanol, $KHCO_3$, and trimethyl iodide ($CH_3I$) under conditions suitable for the methylation of the amine group on N,N-dioleylamine to form the quaternary ammonium compound, N,N-dioeyl-N,N-diemethylammonium chloride.

By "conditions suitable for methylation" is meant, that the reaction occurs at a temperature preferably between 20° C. and 50° C., specifically between 23° C. and 37° C., more specifically 25° C. and 30° C. and reaction times of preferably between about 24–72 hours, specifically 36–50 hours, more specifically 40–48 hours. Those skilled in the art will recognize that the reaction temperature and time may be varied without significantly affecting the reaction. By "about" is meant that the precise time of reaction may be altered without affecting the result of the reaction. For a time period it is generally ±10% or ±2–5%.

Other features and advantages of the invention will be apparent from the following description of the preferred embodiments thereof, and from the claims.

DESCRIPTION OF THE PREFERRED EMBODIMENTS

The drawings will be first described briefly.

DRAWING

The FIGURE is a schematic representation of a process for the synthesis of DODAC.

EXAMPLE 1

Synthesis of N,N-Dioleyl-N,N-Dimethylammonium Chloride (DODAC)

Referring to FIG. 1, Oleylamine (10 g) (Fluka Chemicals) was heated to 140° C. using an oil bath, followed by the rapid addition of oleyl bromide (5 g) (Sigma Chemicals) with constant stirring. The mixture was heated at 140° C. until the disappearance of oleyl bromide (for 30–60 minutes); which was confirmed by thin layer chromatography (TLC) using hexanes for development ($R_f$ ca 0.5) (TLC for visualizing t- and s-amine: 10% methanol in $CH_2Cl_2$, rhodamine or ninhydrin for detection). The mixture was then cooled to room temperature, followed by the addition of 1N NaOH under constant stirring, and the mixture was partitioned between $CH_2Cl_2$ (200 ml) and $H_2O$ (100 ml). The organic layer was washed with brine, dried with $Na_2SO_4$, and evaporated to a syrup. The syrup residue was then dissolved in $CH_2Cl_2$, loaded on the column of $SiO_2$ in $CH_2Cl_2$, followed by elution with 10% ether in $CH_2Cl_2$ (elutes off t-amine which runs faster, 1 g), then 20% ether in $CH_2Cl_2$ followed by methanol which elutes off N,N-dioleylamine (6 g).

Dioleylamine (3 g) was then suspended in methanol (60 ml), $KHCO_3$ (6 g) and $CH_3I$ (3 ml). The mixture was stirred at room temperature for 48 hours, filtered through the Celite pad (Aldrich Chemicals) and the filtered cake was washed well with $CH_2Cl_2$. Filtrate was evaporated to dryness and the solid residue was partitioned between 5% aq. $Na_2S_2O_3$ (100 ml) and $CH_2Cl_2$ (200 ml). The organic layer was then dried ($Na_2SO_4$) and evaporated to a syrup. The syrup was dissolved in methanol-$CH_2Cl_2$ 8:1 and poured on the top of the ion-exchange column AG 1-X2 ($Cl^-$, 100–200 mesh, 100 ml). Elution with methanol-$CH_2Cl_2$ 8:1 afforded DODAC (Quantitative yield).

DODAC is an amphiphilic molecule which can be solubilized with organic solvents or in the presence of a detergent (e.g. Triton X-100, octylglucoside). In the presence of other lipids or individually, it will spontaneously form micelles or liposomes through hydrophobic interaction.

Uses for DODAC

DODAC has several uses including as a delivery agent for anionic macromolecules (e.g. DNA, RNA and protein). DODAC may be used individually or as an aggregate with other lipids or amphipathic molecules. Transfection of cells using these aggregates may be carried out in vitro or in vivo. DODAC can also be used as a pharmaceutical formulation. DODAC can be used to form a liposome for the delivery of drugs, detergents, pharmaceutical or veterinary formulations.

Other embodiments are within the following claims.

What is claimed is:

1. A process for the synthesis of N,N-dioleyl-N,N-dimethylammonium chloride (DODAC) comprising the steps of:
   a) oleylation, wherein oleyl bromide is contacted with oleylamine under conditions suitable for the formation of N,N-dioleylamine; and
   b) methylation of said N,N-dioleylamine from step (a) under conditions suitable for the formation of DODAC.

2. The process of claim 1, wherein said oleylation is carried out at a reaction temperature of between 80° C. and 150° C. for between 30 and 90 minutes.

3. The process of claim 1, wherein said methylation is carried out at a reaction temperature of between 20° C. and 50° C. for between 24 and 72 hours.

4. A process for the synthesis of N,N-dioleyl-N,N-dimethylammonium chloride (DODAC) comprising the steps of:
   a) oleylation, wherein oleyl methone sulfonate is contacted with oleylamine under conditions suitable for the formation of N,N-dioleylamine;
   b) methylation of said N,N-dioleylamine from step (a) under conditions suitable for the formation of DODAC.

5. A process for the synthesis of N,N-dioleyl-N,N-dimethylammonium chloride (DODAC) comprising the steps of:
   a) oleylation, wherein oleyl p-toluene sulfonate is contacted with oleylamine under conditions suitable for the formation of N,N-dioleylamine;
   b) methylation of said N,N-dioleylamine from step (a) under conditions suitable for the formation of DODAC.

6. The process of claim 2, wherein said oleylation is carried out at a reaction temperature of about 150° C.

7. The process of claim 2, wherein said oleylation is carried out at a reaction temperature of about 140° C.

8. The process of claim 2, wherein said oleylation is carried out at a reaction temperature of about 135° C.

9. The process of claim 2, wherein said oleylation is carried out at a reaction temperature of about 145° C.

10. The process of claim 2, wherein said oleylation is carried out for about 60 minutes.

11. The process of claim 2, wherein said olcylation is carried out for about 50 minutes.

12. The process of claim 2, wherein said oleylation is carried out for about 70 minutes.

13. The process of claim 3, wherein said methylation is carried out for about 48 hours.

14. The process of claim 3, wherein said methylation is carried out for about 60 hours.

15. The process of claim 3, wherein said methylation is carried out for about 55 hours.

16. The process of claim 3, wherein said methylation is carried out for about 40 hours.

17. The process of claim 3, wherein said methylation is carried out at room temperature.

18. The process of claim 3, wherein said methylation is carried out at about 25° C.

19. The process of claim 3, wherein said methylation is carried out at about 20° C.

* * * * *